United States Patent [19]
Färm

[11] Patent Number: 6,076,777
[45] Date of Patent: Jun. 20, 2000

[54] POSITIONING DEVICE FOR A MOBILE PHONE

[75] Inventor: Jarmo Färm, Turku, Finland

[73] Assignee: BFE Industries Oy, Turku, Finland

[21] Appl. No.: 09/077,744

[22] PCT Filed: May 9, 1996

[86] PCT No.: PCT/FI96/00262

§ 371 Date: Jun. 11, 1998

§ 102(e) Date: Jun. 11, 1998

[87] PCT Pub. No.: WO96/33885

PCT Pub. Date: Oct. 31, 1996

[30] Foreign Application Priority Data

Jan. 15, 1996 [FI] Finland ................................ 960026 U

[51] Int. Cl.[7] ............................. G12B 9/00; A47B 96/06
[52] U.S. Cl. ........................................ 248/27.1; 248/205.1
[58] Field of Search ................................ 248/27.1, 205.1, 248/220.21, 231.9, 231.85, 231.81, 220.41, 221.11; 312/223.4

[56] References Cited

U.S. PATENT DOCUMENTS

| | | | |
|---|---|---|---|
| 4,805,861 | 2/1989 | Thalenfeld et al. | 248/221.11 |
| 5,651,522 | 7/1997 | Davis et al. | 248/221.11 |

*Primary Examiner*—Ramon O. Ramirez
*Assistant Examiner*—David Heisey
*Attorney, Agent, or Firm*—James C. Lydon

[57] ABSTRACT

An installation device for installing a mobile phone onto the dashboard of a vehicle includes a fastening part attached to the rack of a radio in the dashboard and a supporting part for holding the mobile phone which is connected to the fastening part.

8 Claims, 1 Drawing Sheet

POSITIONING DEVICE FOR A MOBILE PHONE

The invention relates to an installation device for installing a mobile phone onto the dashboard of a vehicle.

In prior art it is known to attach a mobile phone holder right onto the dashboard with screws. This kind of attachment leaves nasty screwmarks on the dashboard.

The above problem has been solved with mounting pieces available for each car make and model, to which mounting piece the actual phone holder is attached. This known solution is based on utilization of existing screws in the dashboard, which are generally not visible but which can be accessed by removing some detachable part like the air vent grate, and the mounting piece is attached to the dashboard with this screw. The disadvantage of this solution is that each car make and model requires its own mounting piece i.e. the mounting piece is according to the car make and model. Also a specific mounting piece must be made for each annual model of the same car. Furthermore, e.g. cars provided with two air cushions or an air conditioning system require a particular solution. After all it is not possible to construct a good workable solution for every car. Generally these mounting pieces are manufactured only for the newest and the most common car models. Manufacturers with the largest selection may have several hundred different mounting piece models which naturally requires maintenance of a large stock. Installation of these known mounting pieces often requires knowledge of the structure of the car and then professional help is needed.

The object of the invention is to provide a mounting piece for mobile phones which suits nearly all car makes and models and additionally to other vehicles and which is easy to install onto the dashboard without screws or any other fasteners.

It has been possible to achieve these objects by an installation device according to the invention, the main characteristics of which appear in the enclosed claims.

The invention is based on the idea that one can utilize the radio rack existing in cars or other vehicles for installing the mobile phone, the rack allowing an easy and firm attachment of the installation device. Radio racks have broadly speaking very similar dimensions and e.g. in the height there may exist deviations of a few millimetres. Thus it is possible to use one and the same installation device nearly in all cars and also other vehicles which have a radio rack.

Thus the invention relates to an installation device for installing a mobile phone onto the vehicle dashboard, the installation device being characterised in that it comprises a fastening part attached or to be attached to the radio rack in the dashboard and a supporting part connected to the fastening part to hold the mobile phone.

According to an advantageous embodiment of the invention said fastening part comprises two parallel elongated arms to be fitted round the rack at the front edges of its two long sides. An intermediate part connects said arms and said supporting part to each other, the arms and the supporting part being situated on the opposite sides of the plane of the intermediate part. The intermediate part may be provided with a slot at the end nearest to the arms allowing adjustment of the distance between the arms. This slot permits installation round racks of various heights. Due to the slot the installation device tightens round the radio rack making installation easy and firm.

Said supporting piece is preferably provided with holes for fastening the holder of the mobile phone. The supporting part itself may serve as the holder of the phone so that the phone may be suspended from the supporting piece using the phone belt clip or the belt clip of the protecting case of the phone.

The installation device according to the invention may also be provided with a wedge-like supplementary part to be attached to the supporting part to enable adjustment of the position of the mobile phone.

The installation device according to the invention may be installed in cars and further in such vehicle groups where previously there was even no interest for non-hole installation like aged vehicles, buses, trucks, working machines, boats and so on.

The installation device according to the invention is preferably made of metal.

The invention will be further described in the following referring to the enclosed drawing in which

DETAILED DESCRIPTION OF THE PREFERRED EMBODIMENTS

Figure 1:
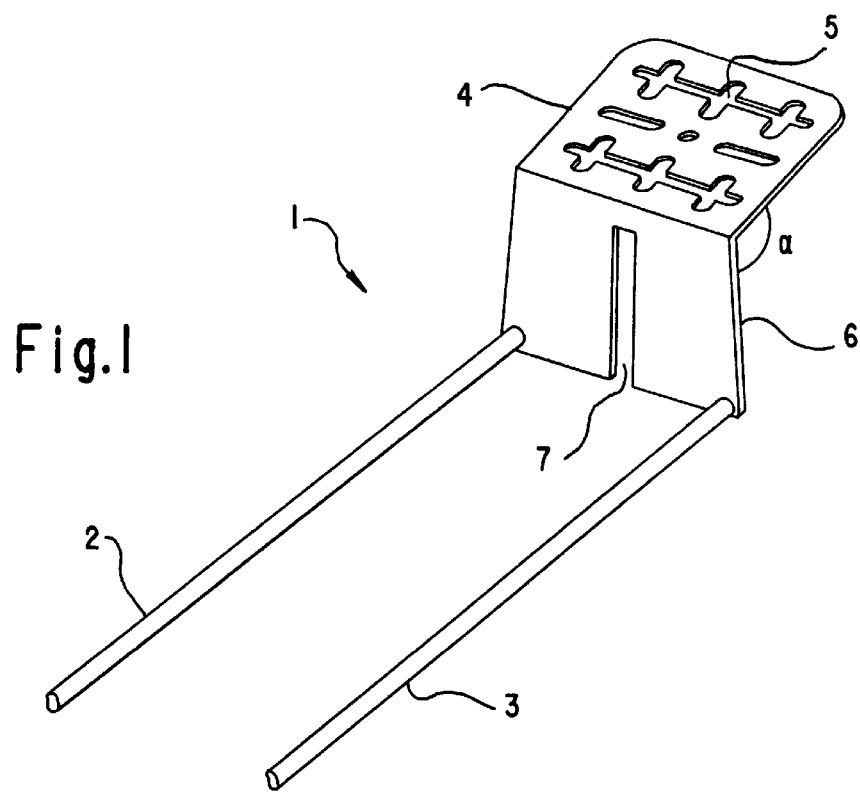
FIG. 1 shows a perspective view of an installation device according to the present invention.

Referring to FIG. 1 the reference number 1 designates the installation device according to the invention. This device has two essentially parallel elongated arms 2 and 3 which are connected at one end to a planar intermediate part 6. The arms 2 and 3 and the intermediate part 6 stand at right angles to each other. A planar supporting part 4 is joined to the opposite end of the intermediate part 6, the supporting part having holes 5 whereby the mobile phone holder (not shown in the figure) can be attached.

Figure 2:
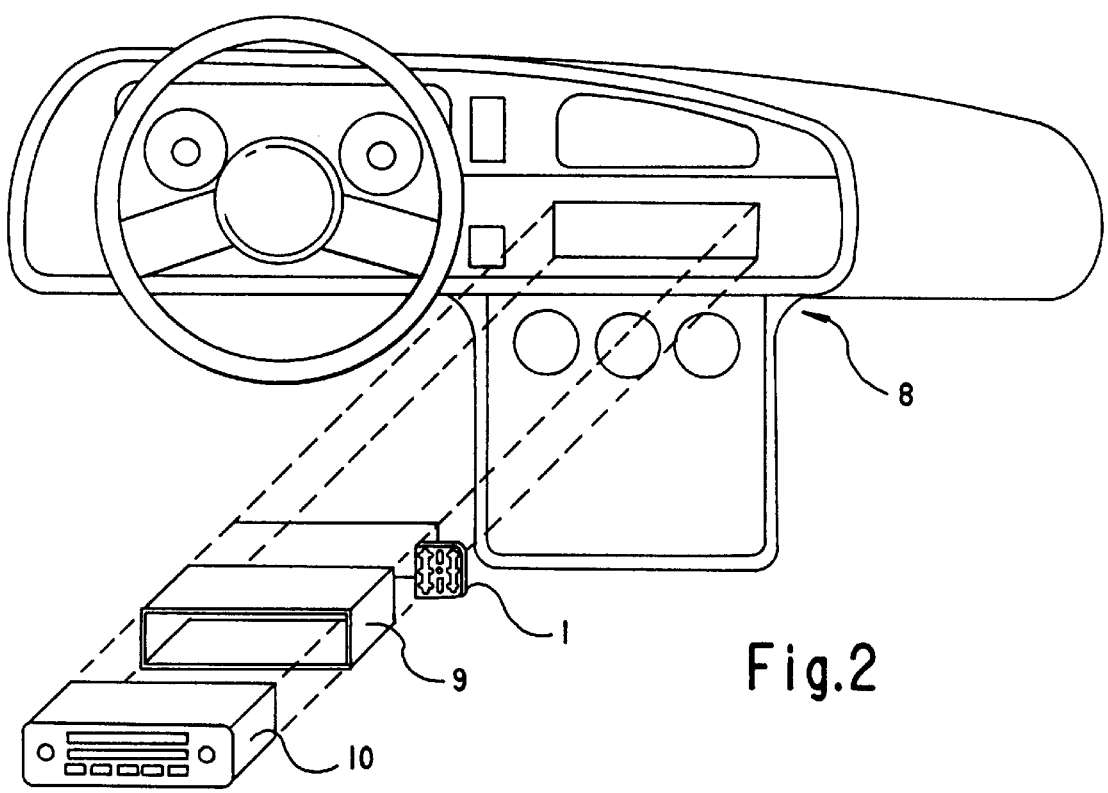
FIG. 2 shows an installation diagram for an installation device according to the present invention.

The distance between the arms 2 and 3 essentially equals the height of the radio rack 9 (see FIG. 2). At the end nearest to the arms the intermediate part 6 is provided with a slot 7 which makes installation possible round racks of various heights. Due to the slot 7 the installation device also tightens round the car radio rack 9 which makes installation easy and firm.

FIG. 1 shows an installation device 1 for right-hand installation. In this case the angle α between the intermediate part 6 and the supporting part 4 is preferably between ca. 90–135°. Installation device suitable for left-hand installation is accomplished by making said angle α smaller e.g. so that it is between ca. 45–90°. The right-hand and the left-hand installation devices can be installed simultaneously thereby providing place for two mobile phones.

Referring to FIG. 2 the installation device according to the invention is installed in the following way: first the car radio 10 is pulled out of the dashboard 8. Then the radio rack, which is normally attached to the dashboard 8 with triangular tongues, is detached and drawn out. Then the installation device according to the invention is fitted round the rack 9 so that the arms prop against the front edges of the rack 9. Finally the rack 9 and the installation device 1 are pushed back into the dashboard 8 and the rack 9 is attached to it with the said tongues. The car radio 10 is finally inserted into its place. Installation of the installation device 1 does not require detaching of electric cables of the car radio 10. Since in most cars the radio has been installed within the reach of the driver, the mobile phone becomes installed in the similar position with the installation device according to the invention.

In the foregoing, only a few advantageous embodiments according to the invention have been disclosed and it is obvious that several variations are possible within the scope of the inventive idea defined by the enclosed claims.

What is claimed is:

1. A mobile phone holder for a vehicle having a dashboard, said mobile phone holder comprising
   a) a substantially planar supporting part adapted to releasably hold a mobile phone;
   b) a fastening part comprising two parallel, elongated arms, wherein
      i) said parallel elongated arms each have a length greater than a length of said supporting part, and
      ii) each of said parallel, elongated arms are adapted to be fitted against a rear end of a rack for holding a radio in said vehicle dashboard, wherein said rack comprises a rectangular-shaped box having a front end into which a radio can be inserted; and
   c) a planar intermediate part having two ends opposite one another, said intermediate part connecting said fastening part and said supporting part, with one end of said intermediate part being connected to said fastening part at an angle of substantially 90°; and the opposite end of said intermediate part being connected to said supporting part.

2. The mobile phone holder of claim 1, wherein said arms are connected to said one end of said intermediate part at a distance from one another, and said distance may be adjusted.

3. The mobile phone holder of claim 2, wherein said supporting part has at least one through-hole for releasably holding a mobile phone.

4. The mobile phone holder of claim 2, wherein said distance between said arms is adapted to be equal to a height of said rack.

5. The mobile phone holder of claim 1, wherein said supporting part has at least one through-hole for releasably holding a mobile phone.

6. The mobile phone holder of claim 1, wherein said supporting part has at least one through-hole for releasably holding a mobile phone.

7. The mobile phone holder of claim 1, wherein an angle between said intermediate part and said supporting part is within a range of from 90 to 135°.

8. The mobile phone holder of claim 1, wherein an angle between said intermediate part and said supporting part is within a range of from 45 to 90°.

* * * * *